(12) United States Patent
Tatara et al.

(10) Patent No.: US 12,220,171 B2
(45) Date of Patent: Feb. 11, 2025

(54) OPHTHALMOLOGIC DEVICE AND OPHTHALMOLOGIC SYSTEM

(71) Applicant: Topcon Corporation, Tokyo (JP)

(72) Inventors: Yoko Tatara, Tokyo (JP); Suguru Miyagawa, Tokyo (JP); Tatsuo Yamaguchi, Tokyo (JP); Makoto Saika, Tokyo (JP)

(73) Assignee: TOPCON CORPORATION, Tokyo (JP)

(*) Notice: Subject to any disclaimer, the term of this patent is extended or adjusted under 35 U.S.C. 154(b) by 501 days.

(21) Appl. No.: 17/665,586

(22) Filed: Feb. 6, 2022

(65) Prior Publication Data
US 2022/0151486 A1    May 19, 2022

Related U.S. Application Data

(63) Continuation of application No. PCT/JP2020/030153, filed on Aug. 6, 2020.

(30) Foreign Application Priority Data

Aug. 16, 2019 (JP) ................................. 2019-149340

(51) Int. Cl.
*A61B 3/00* (2006.01)
*A61B 3/02* (2006.01)
(Continued)

(52) U.S. Cl.
CPC ............ *A61B 3/103* (2013.01); *A61B 3/0285* (2013.01); *A61B 3/1015* (2013.01); *A61B 3/152* (2013.01)

(58) Field of Classification Search
CPC .......... A61B 3/0075; A61B 3/10; A61B 3/00; A61B 3/14; A61B 3/02; A61B 13/00
(Continued)

(56) References Cited

U.S. PATENT DOCUMENTS 5,812,241 A    9/1998 Doms et al.
9,462,939 B2   10/2016 Abitbol et al.
(Continued)

FOREIGN PATENT DOCUMENTS

JP    2001-346762 A    12/2001
JP    2004-535881 A    12/2004
(Continued)

OTHER PUBLICATIONS

Extended European search report issued on May 15, 2023, in corresponding European patent Application No. 20853658.1, 7 pages.
(Continued)

*Primary Examiner* — Dawayne Pinkney
(74) *Attorney, Agent, or Firm* — XSENSUS LLP

(57) ABSTRACT

The ophthalmologic device to be coupled to a correcting device for correcting subject eyes, the correcting device including a right-left pair of two examination windows and a right-left pair of arrangement mechanisms that each arrange first optical elements, includes: a coupling member configured to be detachably coupled to each of coupled members provided on a side surface of the correcting device on a side opposite to an eyepiece side for each subject eye; a second optical element arranged at a position facing a second examination window opposite to a first examination window which is an eyepiece window, when the coupling member is coupled to the coupled member, the second optical element configured to branch a second optical path from a first optical path along the optical axes; and an objective measuring system arranged on the second optical path and configured to acquire ocular characteristics of each subject eye.

8 Claims, 11 Drawing Sheets

(51) Int. Cl.
*A61B 3/028* (2006.01)
*A61B 3/10* (2006.01)
*A61B 3/103* (2006.01)
*A61B 3/12* (2006.01)
*A61B 3/15* (2006.01)

(58) Field of Classification Search
USPC ........ 351/208, 200, 203, 205, 206, 209–211, 351/221–223, 237–239, 246; 600/558
See application file for complete search history.

(56) References Cited

U.S. PATENT DOCUMENTS

| | | | |
|---|---|---|---|
| 2004/0174495 A1* | 9/2004 | Levine | A61B 3/103 351/205 |
| 2004/0218142 A1 | 11/2004 | Wakil et al. | |
| 2005/0243276 A1* | 11/2005 | Van Heugten | A61B 3/103 351/205 |
| 2008/0246921 A1 | 10/2008 | Mihashi et al. | |
| 2012/0092620 A1 | 4/2012 | Epitropoulos | |
| 2012/0188512 A1* | 7/2012 | Duston | A61B 3/028 351/233 |
| 2013/0182224 A1 | 7/2013 | Schwiegerling et al. | |
| 2015/0042957 A1 | 2/2015 | Abitbol et al. | |
| 2017/0135572 A1 | 5/2017 | Takii et al. | |
| 2019/0099076 A1 | 4/2019 | Fujikado et al. | |
| 2023/0165457 A1* | 6/2023 | Takii | A61B 3/103 351/200 |

FOREIGN PATENT DOCUMENTS

| | | |
|---|---|---|
| JP | 2008-246153 A | 10/2008 |
| JP | 2014-030573 A | 2/2014 |
| JP | 2017-086654 A | 5/2017 |
| JP | 2017-169601 A | 9/2017 |

OTHER PUBLICATIONS

English Translations of International Search Report mailed on Oct. 20, 2020, corresponding PCT/JP2020/030153, 2 pages.
English Translations of International Preliminary Report on Patentability (Chapter I) issued on Feb. 17, 2022, corresponding PCT/JP2020/030153, 6 pages.
Japanese Office Action issued Jun. 6, 2024, in Japanese Patent Application No. 2021-540723 counterpart to the above-identified application, 13pp.
Office Action issued on Jul. 5, 2024 in the counterpart Chinese Patent Application No. 202080056396.5, 15pp.

* cited by examiner

OPHTHALMOLOGIC DEVICE AND OPHTHALMOLOGIC SYSTEM

CROSS-REFERENCE TO RELATED APPLICATIONS

The present application is a Continuation of PCT International Application No. PCT/JP2020/030153 filed on Aug. 6, 2020 claiming priority under 35 U.S.C. § 119(a) to Japanese Patent Application No. 2019-149340 filed on Aug. 16, 2019. Each of the above applications is hereby expressly incorporated by reference, in its entirety, into the present application.

BACKGROUND OF THE INVENTION

1. Field of the Invention

The present invention relates to an ophthalmologic device that acquires ocular characteristics of a subject eye and an ophthalmologic system including the ophthalmologic device.

2. Description of the Related Art

In ophthalmologic clinics and optician's stores, a visual target presenting device and a pair of right and left phoropters (correcting device) are installed for subjective examination of visual functions such as an eyesight of a subject eye or eyes (see Japanese Patent Application Laid-Open No. 2001-346762, hereinafter referred to as Patent Literature 1). The visual target presenting device presents a visual target chart, such as a Landolt ring, to the subject eye. Each phoropter has an examination window formed therein, and also rotatably incorporates a lens disk having a plurality of trial lenses that are different in power. Each phoropter arranges one or more trial lenses at a position corresponding to the examination window by rotating the lens disk. In subjective examination of the eyesight of a subject eye or eyes, a subject answers the questions made by an examiner while viewing a visual target chart presented by the visual target presenting device through one of or both the right and left examination windows.

In each phoropter, the type (power) of a trial lens that is first arranged at the position corresponding to the examination window is determined based on the result of measurement by an ophthalmologic device, such as a wavefront sensor, which performs objective measurement of ocular characteristics such as eye refractivity of a subject eye (see Japanese Patent Application Laid-Open No. 2017-169601 and Japanese Patent Application Laid-Open No. 2014-30573, hereinafter referred to as Patent Literatures 2 and 3). The ophthalmologic device can be integrated with each phoropter as described in U.S. Pat. No. 9,462,939 (hereinafter referred to as Patent Literature 4), for example.

CITATION LIST

Patent Literature 1: Japanese Patent Application Laid-Open No. 2001-346762
Patent Literature 2: Japanese Patent Application Laid-Open No. 2017-169601
Patent Literature 3: Japanese Patent Application Laid-Open No. 2014-30573
Patent Literature 4: U.S. Patent No. 9462939

SUMMARY OF THE INVENTION

Incidentally, when an ophthalmologic device that performs objective measurement is not integrated with each phoropter, an examiner is required to enter the result of measurement performed by the ophthalmologic device to a controller of each phoropter, and it is not possible to directly enter the result of the measurement from the ophthalmologic device to the controller. In this case, the ophthalmologic device cannot measure the ocular characteristics of the subject eye, which views the visual target chart through the examination window, continuously in real time. Furthermore, the ophthalmologic device cannot feedback the result of the measurement to each phoropter (controller).

Meanwhile, in the case of using a phoropter system in which an ophthalmologic device and each phoropter are integrated as described in Patent Literature 4, existing phoropters need to be replaced with the phoropter system or the phoropter system needs to be introduced separately, which is not practical from a cost perspective, even if the aforementioned problems could be solved. In addition, although respective users have different needs such as necessity or unnecessity of an ophthalmologic device, the phoropter system described in Patent Literature 4 cannot omit the ophthalmologic device, and therefore it is not possible to meet the needs of users who do not need the ophthalmologic device.

The present invention has been made in light of such circumstances, and aims to provide an ophthalmologic device that can be used integrally with an existing correcting device as necessary, and an ophthalmologic system including the ophthalmologic device.

In order to accomplish the object, an ophthalmologic device of the present invention is an ophthalmologic device to be coupled to a correcting device configured to correct a visual function of subject eyes, the correcting device including a right-left pair of two examination windows arranged along respective optical axes and a right-left pair of arrangement mechanisms that each arrange one or more first optical elements between the two examination windows, the ophthalmologic device including: a coupling member configured to be detachably coupled to each of coupled members which are provided on a side surface of the correcting device on a side opposite to an eyepiece side for each subject eye; a second optical element arranged at a position facing, out of the two examination windows in each right and left pair, a second examination window opposite to a first examination window which is an eyepiece window for each subject eye, in a case where the coupling member is coupled to the coupled member, the second optical element configured to branch a second optical path from a first optical path along the optical axes; and an objective measuring system arranged on the second optical path and configured to acquire ocular characteristics of each subject eye.

Since the ophthalmologic device may be detachably coupled to the coupled member of the correcting device, the ophthalmologic device can be used integrally with an existing correcting device as necessary.

In the ophthalmologic device according to another aspect of the present invention, the coupling member is detachably coupled to the second examination window as the coupled member.

The ophthalmologic device according to another aspect of the present invention includes a housing which is configured to house the second optical element and the objective measuring system, and used as a substitute for a rear cover in a case where the coupling member is coupled to each of the second examination windows in a state where the rear cover which forms a side surface of the correcting device on a side where each of the second examination windows is provided, is detached from the correcting device. Thus, the housing of the ophthalmologic device may be used as the rear cover of the correcting device.

In the ophthalmologic device according to another aspect of the present invention, the second optical element is arranged on an optical axis for each of the right and left optical axes, and the second optical elements are configured to branch the second optical paths from the first optical paths in directions which are parallel to a plane containing both the optical axes and in which second optical paths are away from each other. Thus, it is possible to prevent interference between the right and left of the ophthalmologic device in a case where both eyes of the subject eyes converge.

The ophthalmologic device according to another aspect of the present invention includes an output unit configured to output a result of the ocular characteristics acquired by the objective measuring system to a drive control unit configured to control drive of each of the arrangement mechanisms. This allows the acquisition result of the ocular characteristics by the objective measuring system to be fed back to the correcting device so as to swiftly change each of the first optical element arranged on the optical axis.

The ophthalmologic device according to another aspect of the present invention includes: an observing system configured to acquire an observation image of an anterior eye part of each subject eye; and an alignment detecting unit configured to detect relative positional relationship between each subject eye and the ophthalmologic device based on the observation image acquired by the observing system. This allows the ophthalmologic device to automatically detect alignment with the subject eye.

The ophthalmologic device according to another aspect of the present invention includes an alignment control unit connected to a relative moving mechanism that moves one of each subject eye and the correcting device relatively to the other, the alignment control unit configured to drive the relative movement mechanism based on a detection result of the alignment detecting unit so as to perform alignment of the ophthalmologic device with respect to the subject eye. This allows the ophthalmologic device to automatically achieve alignment with the subject eye.

An ophthalmologic device in order to accomplish the object of the present invention includes: a correcting device configured to correct a visual function of each subject eye, the correcting device including a right-left pair of two examination windows arranged along respective optical axes, and a right-left pair of arrangement mechanisms which each arrange one or more first optical elements between the two examination windows; and the ophthalmologic device.

The present invention makes it possible to use the ophthalmologic device integrally with an existing correcting device as necessary.

DESCRIPTION OF THE PREFERRED EMBODIMENTS

First Embodiment

<Configuration of Ophthalmologic System>

Figure 1:
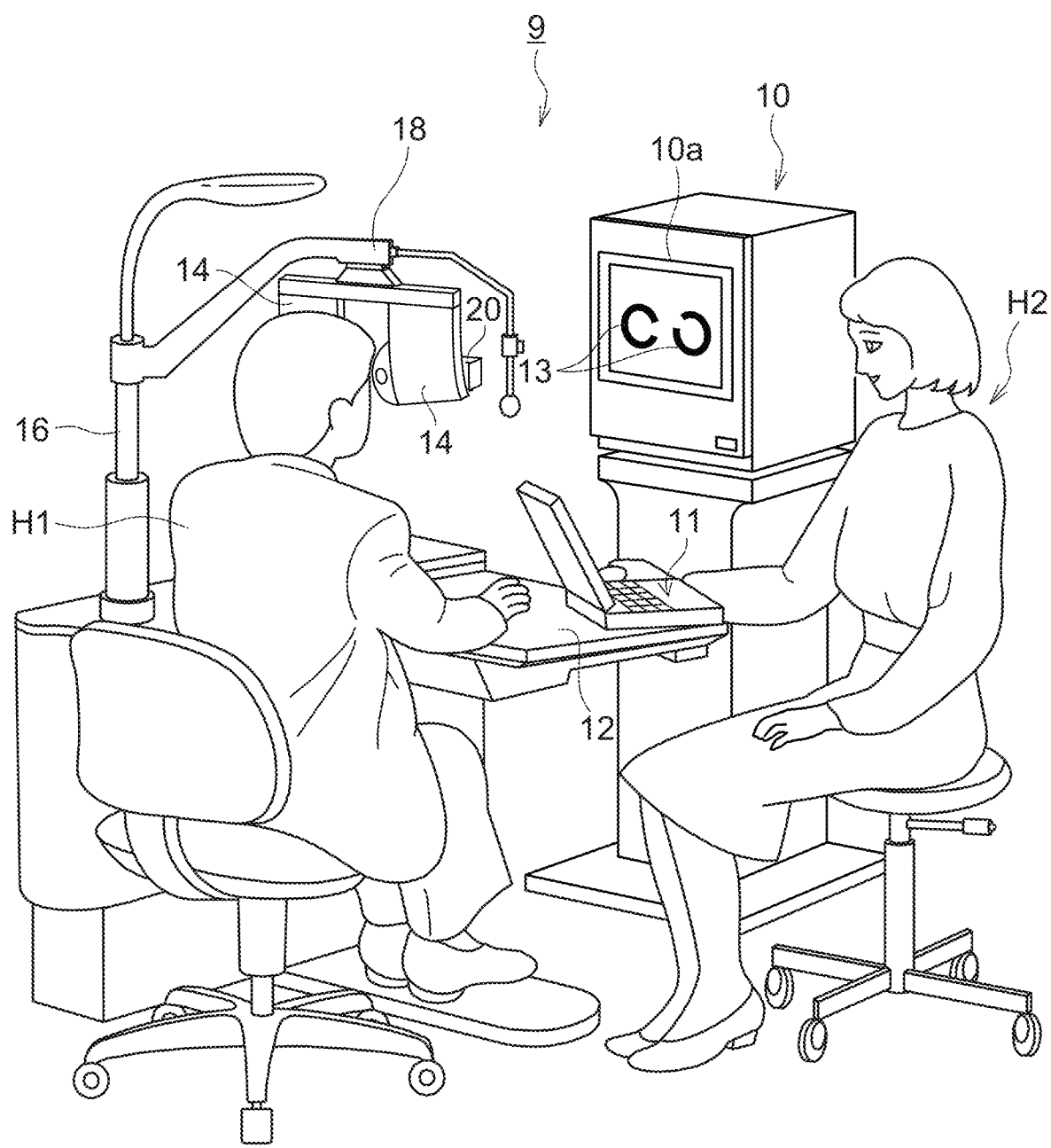
FIG. 1 is an external perspective view of an ophthalmologic system.

FIG. 1 is an external perspective view of an ophthalmologic system 9. As shown in FIG. 1, the ophthalmologic system 9 is used to determine prescription values of power of spectacle lenses or the like to be worn by a subject H1. The ophthalmologic system 9 includes a visual target presenting device 10, a controller 11, an optometry table 12, and a right-left pair of phoropters 14. In addition, the ophthalmologic system 9 includes a right-left pair of wavefront sensors 20 (see FIG. 2) used for objective measurement of the ocular characteristics of subject eyes E.

The visual target presenting device 10 is used for subjective examination of the visual function such as eyesight and the like of the subject eyes E (see FIG. 3) of the subject H1. The visual target presenting device 10 is fixedly installed on an opposite side of the subject H1 with respect to the optometry table 12. The visual target presenting device 10 may be arranged on the optometry table 12. Under the control of the controller 11, the visual target presenting device 10 presents a variety of visual target charts 13 to the subject eyes E through a display window 10a. Since the configuration of the visual target presenting device 10 is a known technology, detailed description thereof is omitted herein.

The optometry table 12 is arranged between the subject H1 and the visual target presenting device 10. The optometry table 12 is freely elevatable in a vertical direction, so that a vertical height position is adjusted to match the body size of the subject H1. This allows the subject H1 to stabilize his/her posture by positioning his/her elbow on an upper surface of the optometry table 12. On the upper surface of the optometry table 12, the controller 11 is arranged and a pole 16 is fixed.

At an upper part of the pole 16, an arm 18 is provided so as to extend in a lateral direction (horizontal direction). The right-left pair of phoropters 14 (also referred to as a reflector head) is suspended from and fixed to a tip part of the arm 18.

The right-left pair of phoropters 14 correspond to the correcting device of the present invention. The phoropters 14 are individually provided for both eyes of the subject eyes E (see FIG. 3). Under control of the controller 11, the phoropters 14 correct visual function of the subject eyes E by arranging trial lenses 24b (see FIG. 3) or the like in front of the subject eyes E as appropriate. The subject H1 answers questions from an examiner H2 while viewing the visual target chart 13 through examination windows 22 and 23 (see FIG. 3) in one of or both the right and left phoropters 14.

Upon reception of input operation by the examiner H2, the controller 11 controls the drive of the visual target presenting device 10, each of the phoropters 14, and each of the wavefront sensors 20 based on the input operation.

Figure 2:
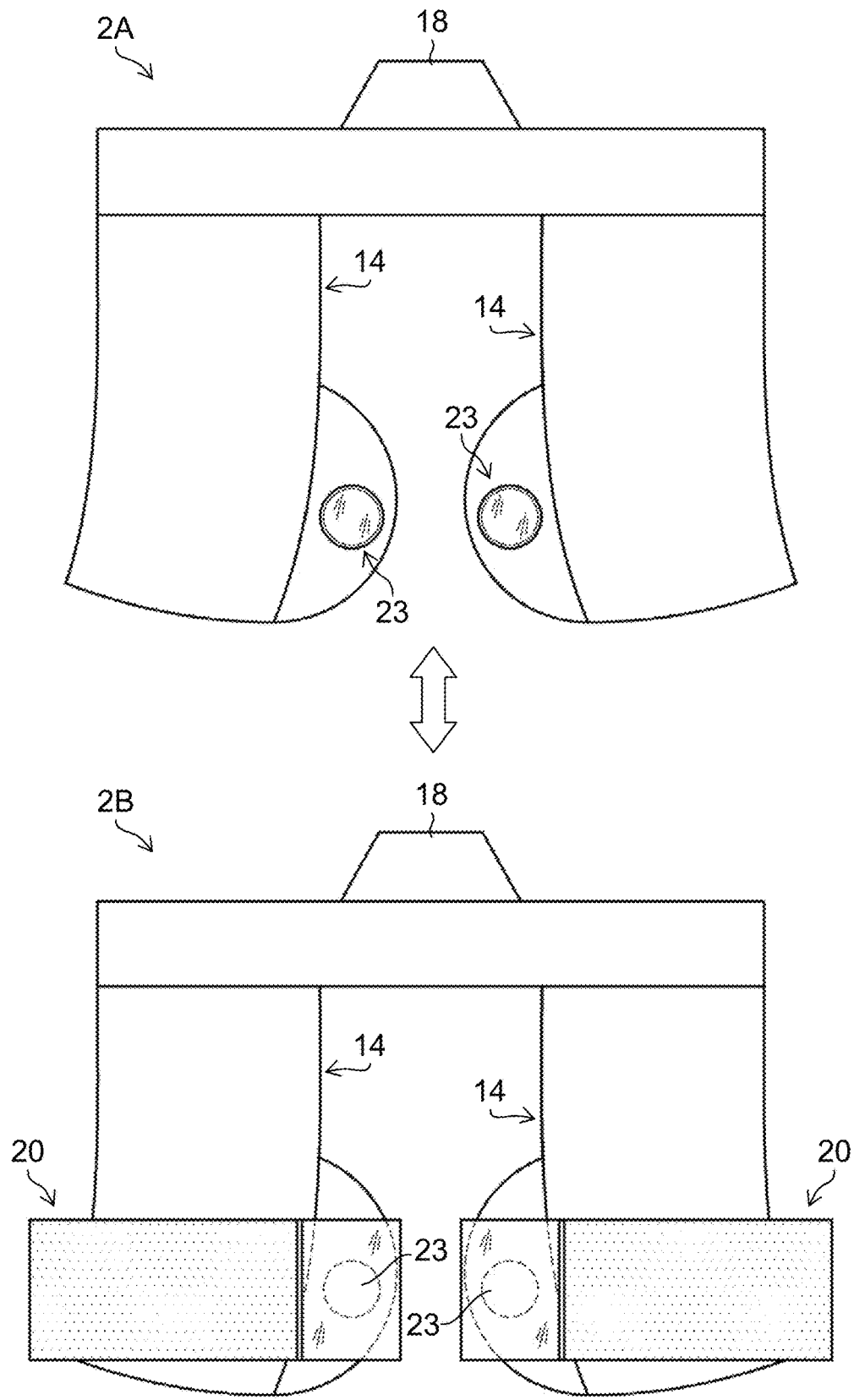
FIG. 2 is a front view of right and left phoropters viewed from a side that faces a visual target presenting device, i.e., the side opposite to a side that faces a subject.

FIG. 2 is a front view of the right and left phoropters 14 viewed from a side that faces the visual target presenting device 10, i.e., the side opposite to a side that faces the subject H1. As shown in FIG. 2, the second examination windows 23 that are opposite to the first examination windows 22 on the eyepiece side in each of the phoropters 14 (see FIG. 3) are each independently and detachably coupled to the wavefront sensors 20 for measuring the ocular characteristics of the subject eye E. Accordingly, in the case of conducting only the subjective examination of eyesight of the subject eyes E, the wavefront sensors 20 are removed from the corresponding phoropters 14 (see reference numeral 2A in FIG. 2). On the contrary, in the case of conducting the subjective measurement using the measurement result of the objective examination of the ocular characteristics of the subject eyes E, the wavefront sensors 20 are coupled to the second examination windows 23 of the respective phoropters 14 (see reference numeral 2B in FIG. 2). Furthermore, only the subjective examination may be conducted in a state where the wavefront sensors 20 are coupled to the respective phoropters 14.

<Phoropters>

Figure 3:
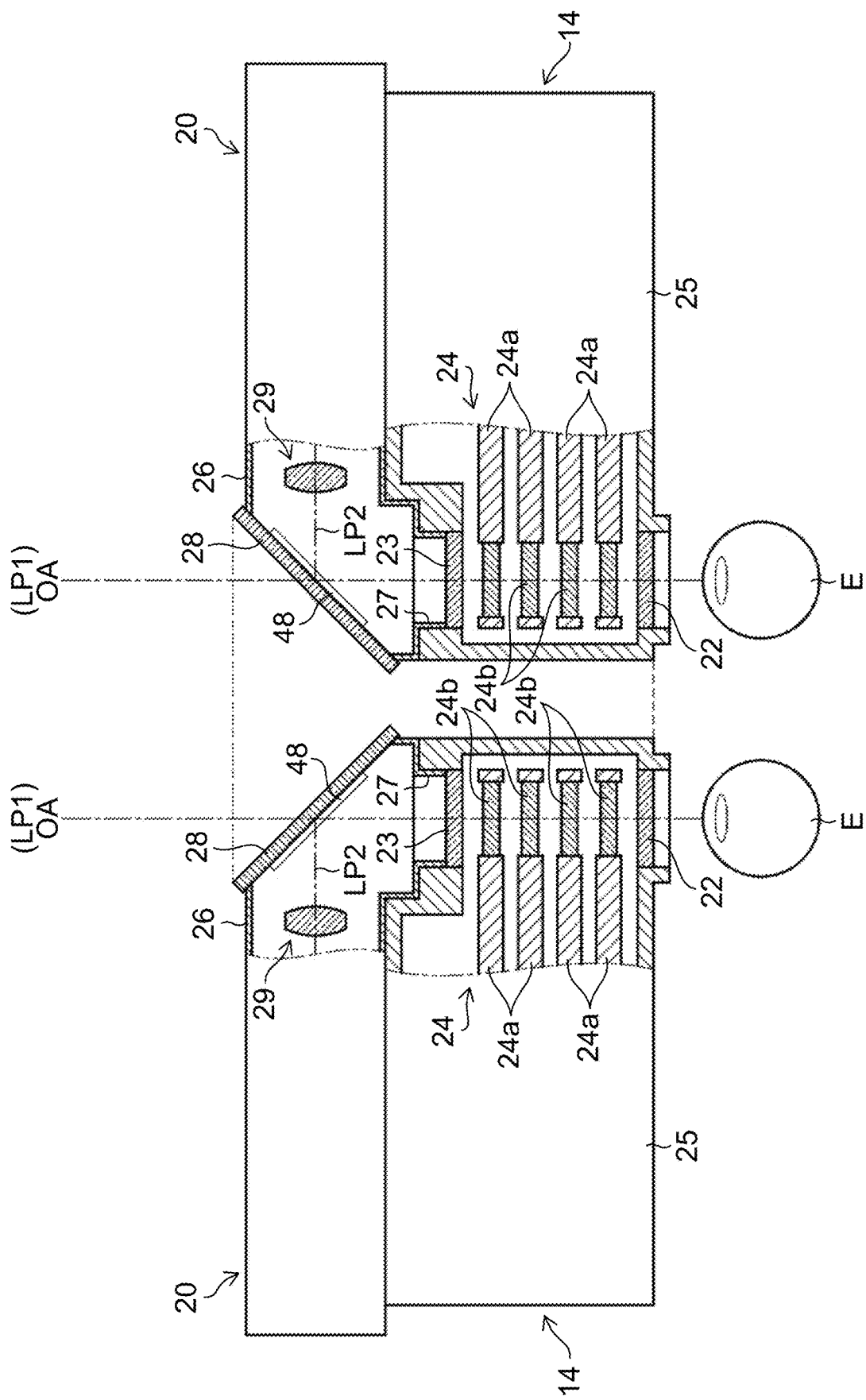
FIG. 3 is a sectional view of the right and left phoropters after wavefront sensors are coupled.
Figure 4:
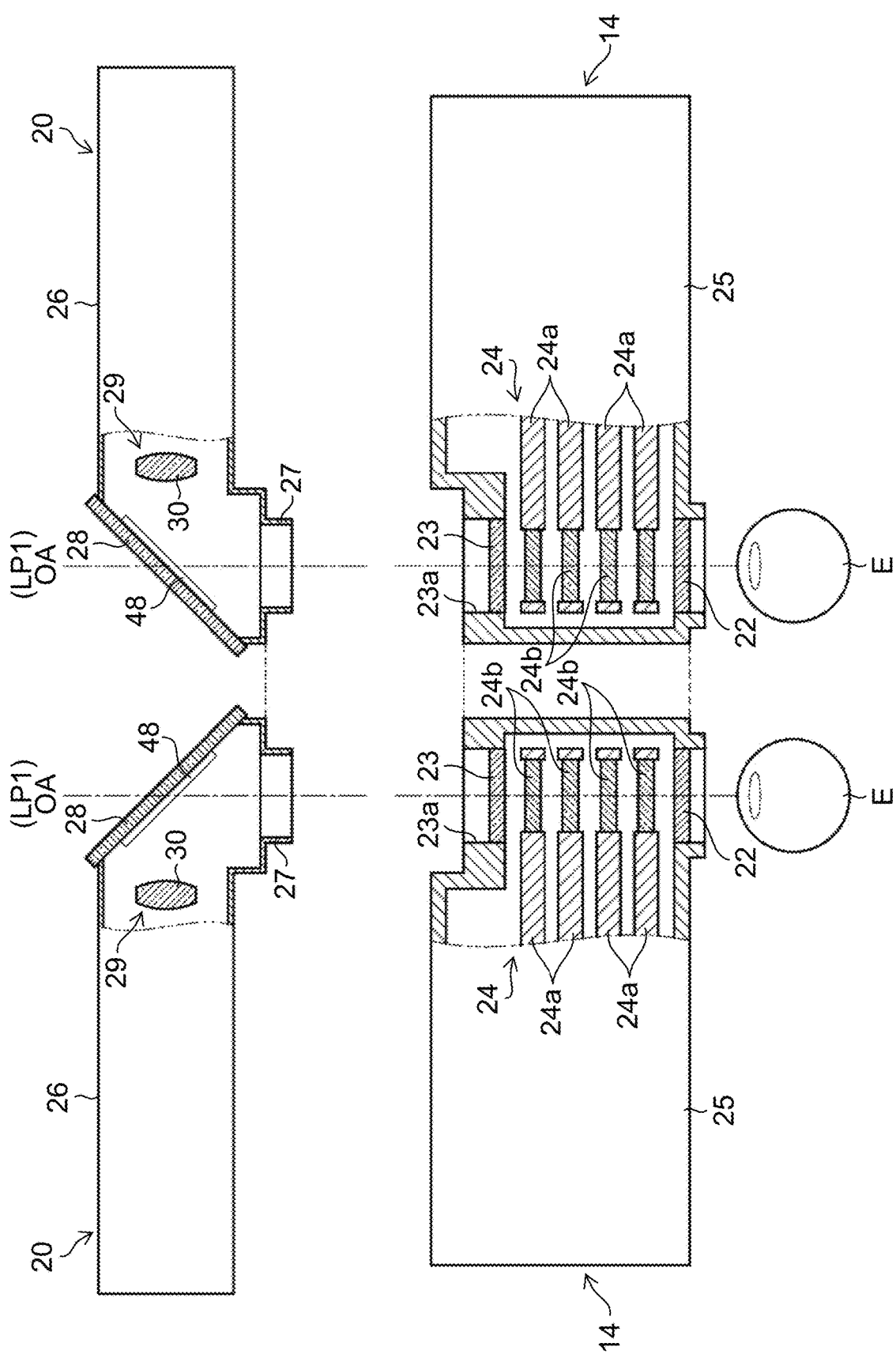
FIG. 4 is a sectional view of the right and left phoropters before the wavefront sensors are coupled.

FIG. 3 is a sectional view of the right and left phoropters 14 after the wavefront sensors 20 are coupled thereto. FIG. 4 is a sectional view of the right and left phoropters 14 before the wavefront sensors 20 are coupled thereto. As shown in FIGS. 3 and 4, the phoropters 14 have the same configuration as existing devices. The phoropters 14 each include an optical axis OA, the first examination window 22 and the second examination window 23 arranged along the optical axis OA, a rotating disk mechanism 24, and a phoropter housing 25. Here, since each of the phoropters 14 has a symmetrical structure, the configuration of one of the phoropters 14 is described herein.

The optical axis OA, which is the optical axis of the first examination window 22, the second examination window 23, and optical elements, is parallel to an anteroposterior direction (back-forth direction) (working distance direction) from the subject H1 to the visual target presenting device 10.

The first examination window 22 and the second examination window 23, which correspond to the two examination windows of the present invention, are provided along the optical axis OA with an interval therebetween. The first examination window 22 is an eyepiece examination window for the subject eye E. The first examination window 22 is provided on a front side surface, which is on a side facing the subject eye E, of the phoropter housing 25. The second examination window 23 is provided on a rear side surface, which is on a side opposite to the side facing the subject eye E (the side opposite to the visual target presenting device 10), of the phoropter housing 25. The second examination window 23 (opening part 23a, see FIG. 4) functions as the coupled member of the present invention. Here, in FIGS. 2 and 3, transparent panels are used as examples of the examination windows 22 and 23. However, the examination windows 22 and 23 may be open holes.

The rotating disk mechanism 24, which corresponds to the arrangement mechanism of the present invention, is housed in the phoropter housing 25. The rotating disk mechanism 24 includes a plurality of lens disks 24a and a motor drive mechanism not illustrated. The lens disks 24a are each formed into a disk shape. The lens disks 24a are each rotatably held by a rotation shaft not illustrated that extends in a direction parallel to the optical axis OA (anteroposterior direction).

The lens disks 24a each include a plurality of types of trial lenses 24b (corresponding to the first optical element of the present invention) different in power and at least one opening hole (not illustrated). In each lens disk 24a, the trial lenses 24b and the at least one opening hole are provided along a circumference of the lens disk 24a. Without being limited to the trial lenses 24b, the first optical elements of the present invention include various optical elements such as pinholes, Maddox lenses, red-green filters, shield plates, cross cylinders, and polarizing plates. The lens disks 24a each rotate around the rotating shaft (not illustrated) so as to selectively arrange any one of the plurality of types of trial lenses 24b or an opening hole on the optical axis OA.

Under control of the controller 11, the motor drive mechanism (not illustrated) rotates each of the lens disks 24a around the rotating shaft (not illustrated). Consequently, one or more trial lenses 24b, or the like, are arranged between the first examination window 22 and the second examination window 23. Here, since the motor drive mechanism is a publicly known technology (see, for example, Patent Literature 1), detailed description of the motor drive mechanism is omitted.

<Wavefront Sensor>

The right and left wavefront sensors 20 constitutes the ophthalmologic device of the present invention together with the controller 11. The wavefront sensors 20 each include a sensor housing 26, a dichroic mirror 28, and a wavefront sensor body 29. Here, since each of the wavefront sensors 20 has a symmetrical structure, the configuration of one of the wavefront sensors 20 is described herein.

The sensor housing 26 holds the dichroic mirror 28 and also houses the wavefront sensor body 29. In addition, a cylindrical coupling member 27 is provided on the front side surface, which is on a side facing the phoropter 14, of the sensor housing 26. Further, the dichroic mirror 28 is held on the rear side surface, which is on a side facing the visual target presenting device 10, of the sensor housing 26, in the state where the dichroic mirror 28 is inclined with respect to the optical axis OA.

The coupling member 27 is made of, for example, a metal material or a hard resin material so as to have a shape that allows detachable coupling to the opening part 23a of the second examination window 23 of the phoropter 14. Note that the coupling member 27 may be integrally formed with the sensor housing 26, or the coupling member 27 formed separately from the sensor housing 26 may be fixed or coupled (connected) to the sensor housing 26. The coupling member 27 is coupled (fitted) to the opening part 23a, so that the wavefront sensor 20 is coupled and held to the phoropter 14.

Inside the coupling member 27, an infrared light source 99 (see FIG. 5) is provided at a position that does not hinder visual recognition of the visual target chart 13 by the subject eye E and that does not interfere with measurement by the wavefront sensor body 29 as described later. The infrared light source 99 emits near-infrared light LA (see FIG. 5) toward the subject eye E through the examination windows 22, 23, the trial lenses 24b, and the like, of the phoropter 14. The wavelength region of the near-infrared light LA is 940 nm to 950 nm, for example. The infrared light source 99 may be provided at a position between the coupling member 27 and the dichroic mirror 28 inside the sensor housing 26 instead of being provided inside the coupling member 27.

The dichroic mirror 28 corresponds to the second optical element of the present invention. The dichroic mirror 28 is held at a position facing the coupling member 27 by the rear side surface of the sensor housing 26 in the state where the dichroic mirror 28 is inclined with respect to the optical axis OA. The dichroic mirror 28 is arranged at the position that is on the optical axis OA and that faces the second examination window 23, in a case where the coupling member 27 is coupled to the opening part 23a. As a result, the dichroic mirror 28 branches a second optical path LP2 from a first optical path LP1 along the optical axis OA.

On the second optical path LP2 branched by the dichroic mirror 28, the wavefront sensor body 29 including an objective lens 30 is provided. Accordingly, the sensor housing 26 has a shape that extends parallel to the second optical path LP2.

Here, the branch directions of the second optical paths LP2 by the right and left dichroic mirrors 28 are set to outward directions which are parallel to the plane containing both the right and left optical axes OA (horizontal plane) and in which the second optical paths LP2 are away from each other. In other words, the right and left wavefront sensors 20 are coupled to the right and left phoropters 14 in such a manner that the branch directions of the second optical paths LP2 by the right and left dichroic mirrors 28 are outward from each other. Thus, the dichroic mirror 28 arranged on the optical axis OA for the left eye side branches the second optical path LP2 leftward from the optical axis OA. The dichroic mirror 28 arranged on the optical axis OA for the right eye side also branches the second optical path LP2 rightward from the optical axis OA.

In the case where the branch directions of the second optical paths LP2 by the respective dichroic mirrors 28 are set to an upward direction or a downward direction, there is a risk of interference between the right and left wavefront sensors 20 when both the phoropters 14 are aligned with both eyes while both the subject eyes E converge. Contrary to this, in the present embodiment, the branch directions of the second optical paths LP2 by the right and left dichroic mirrors 28 are set to the outward direction from each other. Thus, it is possible to reliably prevent interference between the right and left wavefront sensors 20.

In the present embodiment, the second optical path LP2 is perpendicular (including substantially perpendicular) to the first optical path LP1 on the horizontal plane described above. However, the second optical path LP2 may be inclined with respect to the first optical path LP1.

The dichroic mirror 28 in the present embodiment includes an adaptive optical element 48 (adaptive optics (AO)). Note that the adaptive optical element 48 may be omitted.

Figure 5:
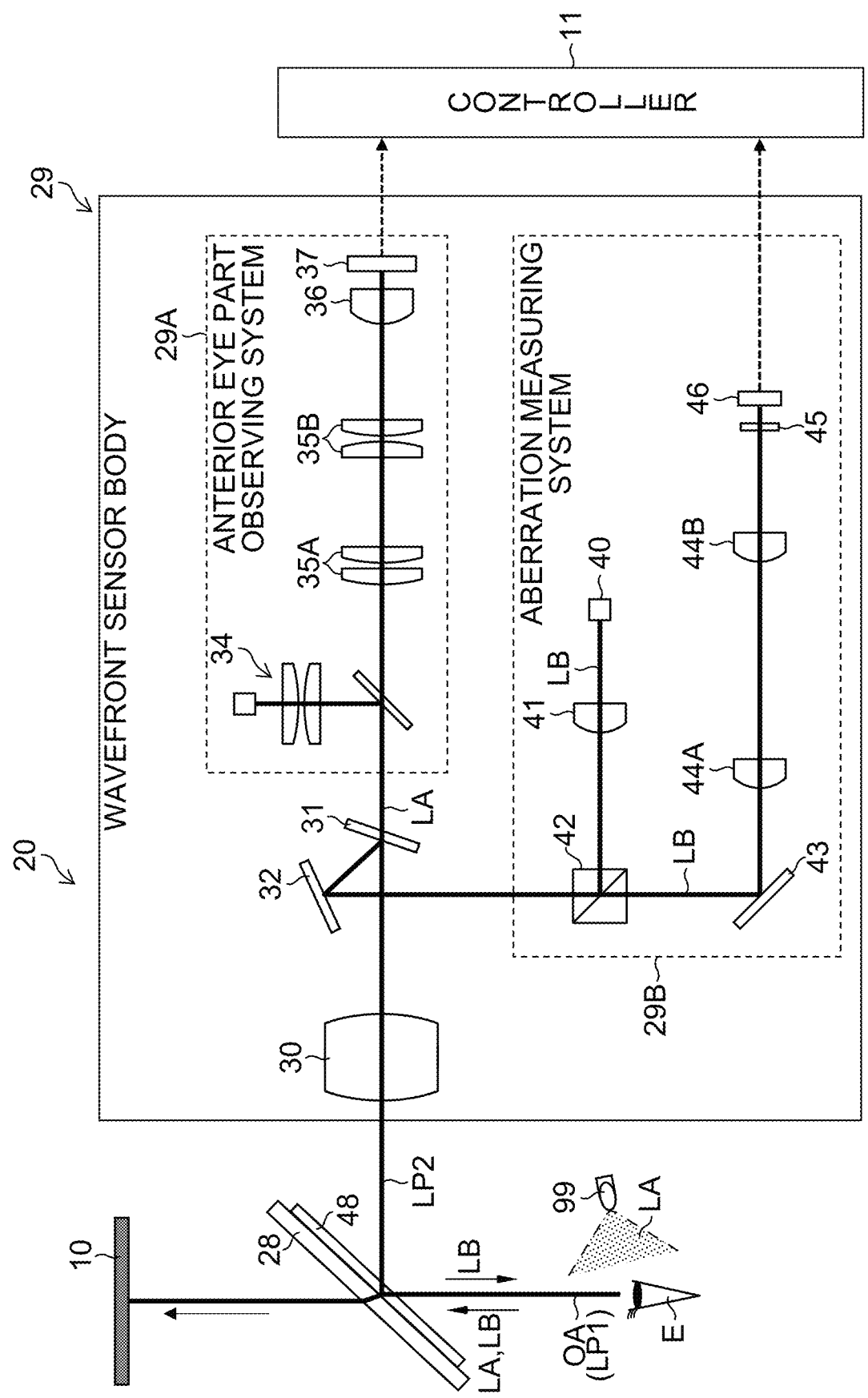
FIG. 5 is a schematic diagram of an optical system of the wavefront sensor corresponding to a right eye of the subject eyes.

FIG. 5 is a schematic diagram of an optical system of the wavefront sensor 20 (dichroic mirror 28 and wavefront sensor body 29) corresponding to the right eye of the subject eyes E. Here, since the optical systems of the right and left wavefront sensors 20 have a symmetrical structure, the structure of the optical system of the wavefront sensor 20 corresponding to the right eye of the subject eyes E is described herein. In FIG. 5, the phoropter 14, the dichroic mirror 28, and the wavefront sensor body 29 are illustrated separately to prevent complication of the drawing.

As shown in FIG. 5, the dichroic mirror 28 allows visible light (wavelength region: about 380 nm to 780 nm) to pass through, and reflects near-infrared light (wavelength region: about 800 nm to 1100 nm) different in wavelength region from the visible light. Specifically, the dichroic mirror 28 reflects near-infrared light LB incident from the later-described wavefront sensor body 29 toward the subject eye E. The dichroic mirror 28 also reflects near-infrared lights LA and LB incident from the subject eye E through the examination windows 22, 23, etc., toward the wavefront sensor body 29. Here, since image light of the visual target chart 13 passes through the dichroic mirror 28, the subject eye E can visually recognize the visual target chart 13.

The wavefront sensor body 29, which is a measuring instrument that can perform continuous measurement, is used to measure the ocular characteristics (wavefront aberration) of the subject eye E. The wavefront sensor body 29 is also used to measure eye positions (visual line direction) of both eyes of the subject eyes E, to measure a convergence angle between both eyes of the subject eyes E, and to observe an anterior eye part (detect pupil diameter and pupil center). The wavefront sensor body 29 emits near-infrared light LB toward the dichroic mirror 28. The wavefront sensor body 29 also receives near-infrared lights LA and LB of two wavelengths which are reflected by the dichroic mirror 28, and outputs reception signals for each wavelength region to the controller 11.

The wavefront sensor body 29 includes an anterior eye part observing system 29A, an aberration measuring system 29B, an objective lens 30, a dichroic mirror 31, and a mirror 32.

The objective lens 30 emits near-infrared light LB with a wavelength of 830 nm to 840 nm, which is incident from the later-described aberration measuring system 29B through the mirror 32 and the dichroic mirror 31, toward the dichroic mirror 28. The near-infrared lights LA and LB of two wavelengths reflected by the subject eye E enter the objective lens 30 via the first optical path LP1, the dichroic mirror 28 and the second optical path LP2. The near-infrared lights LA and LB pass through the objective lens 30 and enter the dichroic mirror 31.

The dichroic mirror 31 allows the near-infrared light LA with a wavelength of 940 nm to 950 nm to pass through, and reflects the near-infrared light LB with a wavelength of 830 nm to 840 nm. Accordingly, the dichroic mirror 31 reflects the near-infrared light LB, which is incident from the later-described aberration measuring system 29B through the mirror 32, toward the objective lens 30. The dichroic mirror 31 also allows the near-infrared light LA, out of the near-infrared lights LA and LB of two wavelengths incident from the objective lens 30, to enter the anterior eye part observing system 29A and reflects the near-infrared light LB toward the mirror 32.

The mirror 32 reflects the near-infrared light LB, which is incident from one of the aberration measuring system 29B and the dichroic mirror 31, toward the other.

The anterior eye part observing system 29A, which corresponds to the observing system of the present invention, receives the near-infrared light LA and acquires an observation image of the subject eye E under the control of the controller 11. The observation image is used for alignment and for measurement (including detection, sensing, examination, and determination) of the eye position (visual line direction), the convergence state, and the pupil diameter of both eyes of the subject eyes E, for example. The anterior eye part observing system 29A includes an alignment optical system 34, relay lenses 35A and 35B, an imaging lens 36, and an imaging element 37 (light receiving element).

The alignment optical system 34 sheds (projects) an alignment luminous flux to the anterior eye part of the subject eye E through the dichroic mirror 31, the objective lens 30, the dichroic mirror 28 and so on. As a result, because a bright spot image is generated in the observation image of the anterior eye part acquired by the imaging element 37 described later, the wavefront sensor 20 can be aligned with the subject eye E. Note that in the first embodiment, alignment is manually performed by the examiner H2.

The relay lenses 35A and 35B emit the near-infrared light LA incident from the dichroic mirror 31 toward the imaging lens 36. The imaging lens 36 images the near-infrared light LA (image light of the anterior eye part), which is incident from the relay lens 35B, on the light receiving surface of the imaging element 37.

The imaging element 37, which is a publicly known area sensor (area image sensor), receives (images) the near-infrared light LA imaged by the imaging lens 36, and outputs to the controller 11 a light receiving signal indicating an observation image of the anterior eye part of the subject eye E.

The aberration measuring system 29B, which constitutes a part of the objective measuring system of the present invention, receives the near-infrared light LB, and outputs a light receiving signal used for measuring eye refractivity or the like of the subject eye E under the control of the controller 11. The aberration measuring system 29B includes: a semiconductor light source 40 such as super luminescent diodes (SLDs) and so on; a collimated lens 41; a polarized beam splitter 42; a mirror 43; lens systems 44A and 44B; a Hartmann plate 45; and an imaging element 46 (light receiving element).

The semiconductor light source 40 emits the near-infrared light LB with a wavelength of 830 nm to 840 nm toward the collimated lens 41. The collimated lens 41 changes the near-infrared light LB, which is incident from the semiconductor light source 40, into a substantially parallel light, and emits the light toward the polarized beam splitter 42. Here, in order to converge the near-infrared light LB at an eye fundus of the subject eye E, the semiconductor light source 40 is moved in accordance with the power of the subject eye E as necessary.

The polarized beam splitter 42 reflects S-polarized light and allows P-polarized light to pass through, for example. The polarized beam splitter 42 reflects the near-infrared light LB incident from the collimated lens 41 toward the mirror 32. As a result, the near-infrared light LB is emitted to the subject eye E via the mirror 32, the dichroic mirror 31, the objective lens 30, the dichroic mirror 28, the phoropter 14 and so on. The near-infrared light LB (return light) reflected by the subject eye E travels backward along the same path as an outbound path and enters the polarized beam splitter 42.

The polarized beam splitter 42 allows the near-infrared light LB incident from the mirror 32 via the dichroic mirror 31 and the like, to pass through as it is, so that the near-infrared light LB is emitted toward the mirror 43.

The mirror 43 reflects the near-infrared light LB that is incident from the polarized beam splitter 42 toward the lens system 44A. The lens systems 44A and 44B emit the near-infrared light LB, which is incident from the mirror 43, toward the Hartmann plate 45.

On the surface of the Hartmann plate 45, a number of microlenses having an equal focal length are formed. The Hartmann plate 45 splits the near-infrared light LB incident from the lens system 44B, into a plurality of luminous fluxes corresponding to the respective microlenses, and each of the luminous fluxes is imaged on the light receiving surface of the imaging element 46. Note that the lens system 44B and the Hartmann plate 45 are moved as necessary so that substantially parallel light enters the Hartmann plate 45 from the lens system 44B. The semiconductor light source 40, the lens system 44B and the Hartmann plate 45 may be moved in conjunction with each other.

The imaging element 46, which is a publicly known area sensor, receives (images) a plurality of luminous fluxes imaged on the light receiving surface by the Hartmann plate 45, and outputs to the controller 11 light receiving signals indicating a plurality of point images (Hartmann images) corresponding to the respective luminous fluxes. This makes it possible to measure the wavefront aberration of the subject eye E, which indicates the ocular characteristics (such as eye refractivity) of the subject eye E.

As the adaptive optical element 48 (also referred to as a wavefront compensation device), liquid crystal on silicon (LCOS) or the like is used, for example. However, the type of the adaptive optical element 48 is not particularly limited. The adaptive optical element 48 is controlled by the controller 11 to remove high-order aberration contained in the near-infrared light LB (return light) received by the imaging element 46 in the aberration measuring system 29B. Here, since the detailed control method is a publicly known technology, the detailed description thereof is omitted herein. In the present embodiment, the adaptive optical element 48 is provided in the dichroic mirror 28. However, the arrangement of the adaptive optical element 48 can be changed as appropriate. The adaptive optical element 48 may be installed between the wavefront sensor 20 and the visual target presenting device 10 to achieve the appearance of the visual target chart 13 as viewed by the subject eye E when the high-order aberration is removed.

<Controller>

Figure 6:
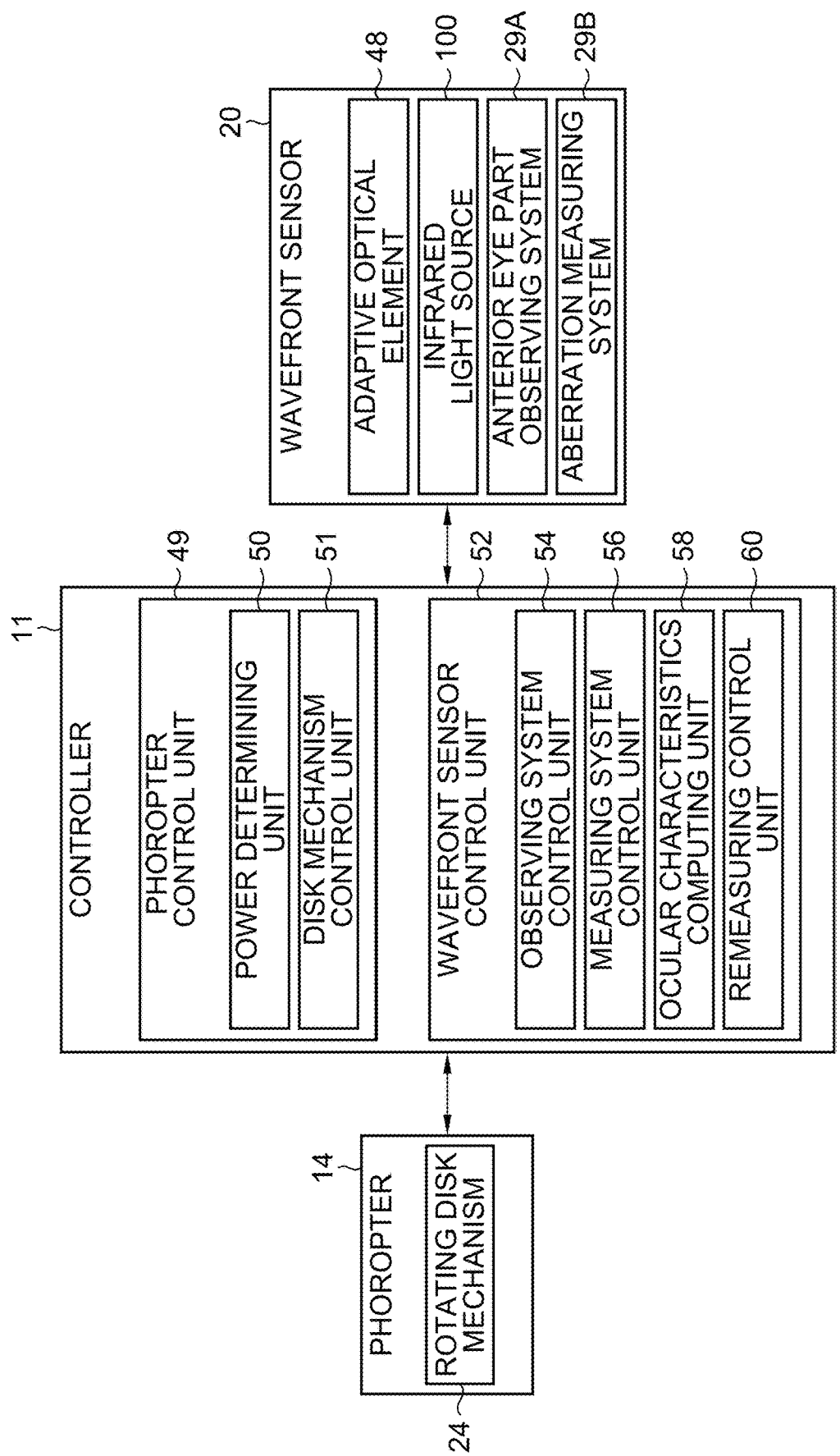
FIG. 6 is a functional block diagram of a controller.

FIG. 6 is a functional block diagram of the controller 11. Here, in FIG. 6, illustration of the visual target presenting device 10 is omitted. As shown in FIG. 6, the controller 11 constitutes a part of the ophthalmologic device of the present invention together with the wavefront sensors 20. The controller 11 is connected to the visual target presenting device 10, the phoropters 14, and the wavefront sensors 20 in a wired and wireless manner. The controller 11 comprehensively controls operation of the respective units. Note that the controller 11 in the present embodiment is formed by adding functions for controlling each of the wavefront sensors 20 and so on, to an existing control device (see Patent Literature 1) that controls the visual target presenting device 10 and the phoropters 14.

The controller 11 includes a computing circuit made up of various processors and memories or the like. Various processors include central processing units (CPUs), graphics processing units (GPUs), application specific integrated circuits (ASICs), and programmable logical devices, such as simple programmable logic devices (SPLDs), complex programmable logic devices (CPLDs), and field programmable gate arrays (FPGAs). Note that the various functions of the controller 11 may be achieved by a single processor, or achieved by a plurality of processors of the same type or different types.

The controller 11 functions as a phoropter control unit 49 and a wavefront sensor control unit 52 by reading and executing programs stored in storage circuits or storage devices not illustrated.

The phoropter control unit 49 includes a power determining unit 50 and a disk mechanism control unit 51.

In the case where the phoropters 14 are coupled to the wavefront sensor 20, the power determining unit 50 determines the power of the trial lens 24*b* that is for correcting the visual function of the subject eyes E based on the result of computing the ocular characteristics (wavefront aberration) of the subject eyes E input from the ocular characteristics computing unit 58 described later. The power includes, for example, spherical power (S: Sphere), cylinder power (C: Cylinder), and an angle of astigmatic axis (A: Axis).

For example, the power determining unit 50 determines power of the trial lens 24b based on secondary aberration of the wavefront aberration, or determines the power of the trial lens 24b based on a best focus, a spot diameter and a minimum root mean square (RMS) wavefront aberration in consideration of the high-order aberration of the wavefront aberration. Here, since the method of determining the power of the trial lens 24b is a publicly known technology, the detailed description thereof is omitted.

In the case where the phoropters 14 are not coupled to the wavefront sensors 20, the power determining unit 50 determines the power of the trial lens 24b for correcting the visual function of the subject eyes E based on input information input into the controller 11 by the examiner H2, such as the result of determining the ocular characteristics (eye refractivity) of the subject eyes E which are separately measured.

The disk mechanism control unit 51, together with the power determining unit 50 described above, constitutes the drive control unit of the present invention. The disk mechanism control unit 51 drives the rotating disk mechanism 24 to arrange one or more trial lenses 24b on the optical axis OA based on the power of the trial lens 24b determined by the power determining unit 50.

The wavefront sensor control unit 52 includes an observing system control unit 54, a measuring system control unit 56, the ocular characteristics computing unit 58 and a remeasuring control unit 60.

The observing system control unit 54 controls each unit in the anterior eye part observing system 29A and the infrared light source 99 to cause the infrared light source 99 to irradiate the subject eyes E with the near-infrared light LA and causes the imaging element 37 to receive the near-infrared light LA (return light). The observing system control unit 54 also displays the observation image of the anterior eye part of the subject eye E on a display unit (not illustrated) of the controller 11.

The measuring system control unit 56 controls the aberration measuring system 29B, the adaptive optical element 48, and the like, to cause the aberration measuring system 29B to irradiate the subject eyes E with the near-infrared light LB, causes the imaging element 46 to receive the near-infrared light LB, and causes the adaptive optical element 48 to remove aberration. The light receiving signal of the near-infrared light LB output from the imaging element 46 is input into the ocular characteristics computing unit 58.

The ocular characteristics computing unit 58, together with the aberration measuring system 29B described above, constitutes the objective measuring system of the present invention. The ocular characteristics computing unit 58 computes the ocular characteristics (wavefront aberration) such as the eye refractivity, or the like, of the subject eyes E by a publicly known method, based on the light receiving signal of the near-infrared light LB input from the imaging element 46. After the ocular characteristics of the subject eyes E are computed, the ocular characteristics computing unit 58 functions as the output unit of the present invention and outputs the computation result of the ocular characteristics to the power determining unit 50. As a result, determination of the power of the trial lens 24b by the power determining unit 50 and driving of the rotating disk mechanism 24 (change of the trial lens 24b) by the disk mechanism control unit 51, are automatically performed.

The remeasuring control unit 60 re-operates the measuring system control unit 56 and the ocular characteristics computing unit 58 in a case where each of the phoropters 14 is coupled to the wavefront sensor 20 and the drive of the rotating disk mechanism 24 is performed. As a result, the aberration measuring system 29B performs irradiation of the subject eyes E with the near-infrared light LB and reception of the near-infrared light LB by the imaging element 46 through the trial lens 24b. The ocular characteristics computing unit 58 also computes the ocular characteristics of the subject eyes E based on the light receiving signal of the near-infrared light LB input from the imaging element 46.

Next, the remeasuring control unit 60 computes residual power by a publicly known method, based on the result of computing the new ocular characteristics of the subject eyes E by the ocular characteristics computing unit 58. The remeasuring control unit 60 then determines whether or not the residual power is within a prescribed range, for example, whether or not S and C are each within ±0.25°. The remeasuring control unit 60 terminates operation in a case where the residual power is within the prescribed range.

On the other hand, the remeasuring control unit 60 outputs the result of computing the residual power to the power determining unit 50 in a case where the residual power is not within the prescribed range. The power determining unit 50 determines the power of the trial lens 24b to be arranged newly on the optical axis OA, based on the power of one or more trial lenses 24b already arranged on the optical axis OA and the residual power, and outputs the determination result to the disk mechanism control unit 51. The disk mechanism control unit 51 then drives the rotating disk mechanism 24 to change the trial lens 24b to be arranged on the optical axis OA.

When the change of the trial lens 24b is completed, the remeasuring control unit 60 causes the measuring system control unit 56 and the ocular characteristics computing unit 58 to re-operate, and performs computation and determination of the residual power. Hereinafter, the remeasuring control unit 60 repeatedly performs output of the computation result of the residual power to the power determining unit 50, re-operation of the measuring system control unit 56 and the ocular characteristics computing unit 58, and computation and determination of the residual power until the residual power is within the prescribed range.

<Alignment of Wavefront Sensors>

In a case where the phoropters 14 are coupled to the wavefront sensors 20, the optical axes OA of the phoropters 14 are aligned with the central shafts of the coupling members 27 of the wavefront sensors 20 in a right-left direction (X direction) and in an up-down direction (Y direction). In addition, when the wavefront sensors 20 rotate around the optical axes OA (Z axes), the results of measuring astigmatic power of the subject eyes E are affected. Hence, the rotation positions of the wavefront sensors 20 are adjusted. The rotation positions are adjusted by using, for example, an astigmatic eye model.

Operation of First Embodiment

Figure 7:
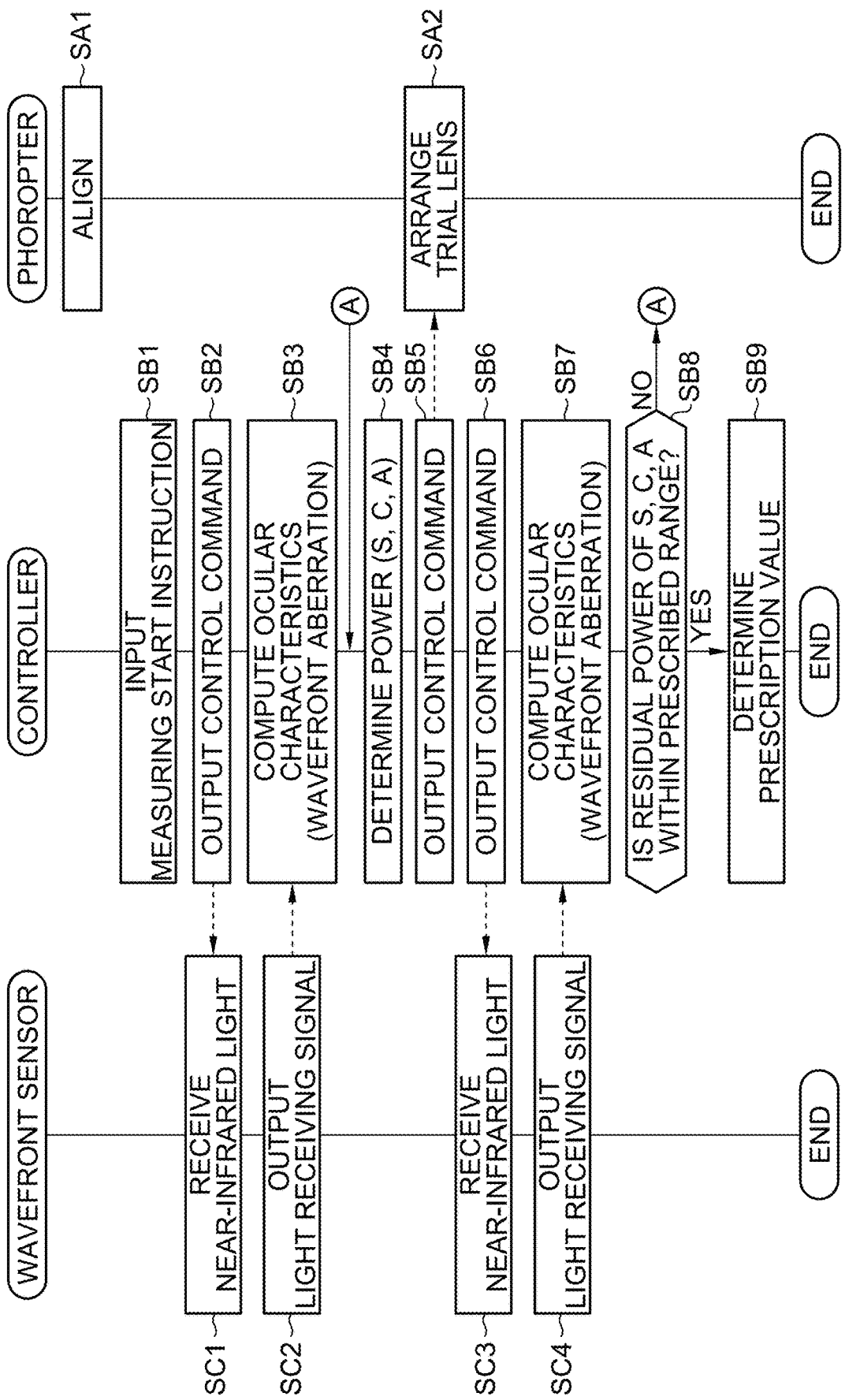
FIG. 7 is a flowchart showing flow of processing of determination processing of a prescription value of an spectacle lens for a subject using the ophthalmologic system.

FIG. 7 is a flowchart showing the flow of determination processing of a prescription value of spectacle lenses for the subject H1 using the ophthalmologic system 9 having the above configuration. As shown in FIG. 7, the examiner H2 first couples the coupling members 27 of the wavefront sensors 20 to the opening parts 23a of the second examination windows 23 of the phoropters 14. Accordingly, the wavefront sensors 20 are coupled to the phoropters 14, respectively.

Upon activation of each of the wavefront sensors 20, radiation of alignment luminous flux to the subject eye E by the alignment optical system 34, radiation of near-infrared light LA to the subject eye E from the infrared light source 99, acquisition of an observation image of the anterior eye part of the subject eye E by the anterior eye part observing system 29A, and display of the observation image by a display unit not illustrated, are performed. Based on the observation image displayed on the display unit and alignment luminous fluxes within the observation image, the examiner H2 manually moves each of the phoropters 14 and performs manual alignment of the wavefront sensors 20 with respect to the subject eye E (step SA1).

When the manual alignment is completed, the examiner H2 inputs a measuring start instruction to the controller 11 (step SB1). Accordingly, the measuring system control unit 56 of the controller 11 outputs, to the aberration measuring system 29B in the wavefront sensor 20 and the adaptive optical element 48, a control command that commands operation of these component members (step SB2). As a result, the radiation of the near-infrared light LB to the subject eye E by the aberration measuring system 29B, the reception of the near-infrared light LB by the imaging element 46 (step SC1), the aberration removal by the adaptive optical element 48, and output of the light receiving signal from the imaging element 46 to the ocular characteristics computing unit 58 of the controller 11 (step SC2) are performed.

When the ocular characteristics computing unit 58 receives the light receiving signal from the imaging elements 46, the ocular characteristics computing unit 58 computes the ocular characteristics (wavefront aberration), such as eye refractivity, of the subject eye E based on the light receiving signal (step SB3). Thus, it is possible to measure the ocular characteristics of the subject eye E which views the visual target chart 13 through the examination windows 22, 23 continuously in real time. The ocular characteristics computing unit 58 then outputs the result of computing the ocular characteristics of the subject eye E to the power determining unit 50.

In a case where the power determining unit 50 receives the result of computing the ocular characteristics from the ocular characteristics computing unit 58, the power determining unit 50 determines the power (S, C, A) of the trial lens 24b based on the result of the computation, and outputs the determination result to the disk mechanism control unit 51 (step SB4). As a result, the disk mechanism control unit 51 outputs to the rotating disk mechanism 24 a control command that commands arrangement of the trial lens 24b based on the power determined by the power determining unit 50 (step SB5). In response to the control command, the rotating disk mechanism 24 is driven to arrange one or more trial lenses 24b on the optical axis OA (step SA2).

In a case where arrangement of the trial lenses 24b is completed, the remeasuring control unit 60 causes the measuring system control unit 56 and the ocular characteristics computing unit 58 to re-operate. As a result, the measuring system control unit 56 outputs control commands again to the aberration measuring system 29B and the adaptive optical element 48 of the wavefront sensor 20 (step SB6). In response to the command, steps such as the reception of the near-infrared light LB by the imaging element 46 (step SC3) and the output of the light receiving signal from the imaging element 46 to the ocular characteristics computing unit 58 (step SC4) are performed.

The ocular characteristics computing unit 58 computes the ocular characteristics (wavefront aberration) of the subject eye E corrected through the trial lenses 24b (step SB7). Thus, it is possible to measure the ocular characteristics of the subject eye E corrected through the trial lenses 24b, continuously and real-timely.

Next, the remeasuring control unit 60 computes residual power based on the new computation result of ocular characteristics of the subject eyes E by the ocular characteristics computing unit 58, and determines whether or not the residual power is within a prescribed range (step SB8). In a case where the residual power is within the prescribed range, the processing proceeds to step SB9 described later (YES in step SB8).

On the other hand, In a case where the residual power is not within the prescribed range (NO in step SB8), the remeasuring control unit 60 outputs the computation result of residual power to the power determining unit 50. Consequently, the power determining unit 50 determines the power of the trial lens 24b newly arranged on the optical axis OA, based on the power of the trial lenses 24b already arranged on the optical axis OA and the residual power (step SB4). Then, the processing of step SB5 and step SA2 described above is repeatedly performed, and the trial lens 24b arranged on the optical axis OA is changed. Thus, in the present embodiment, it is possible to swiftly feedback the measurement result of the ocular characteristics of the subject eye E corrected through the trial lens 24b to the phoropter 14, so as to swiftly change the trial lens 24b arranged on the optical axis OA.

After the trial lens 24b is changed, the remeasuring control unit 60 causes the measuring system control unit 56 and the ocular characteristics computing unit 58 to re-operate. Consequently, the processing of steps SB6, SC3, SC4, and SB7 described above are repeatedly performed. The remeasuring control unit 60 then determines whether or not the residual power is within the prescribed range (step SB8). Hereinafter, a series of the processing described before is repeated until the remeasuring control unit 60 determines that the residual power is within the prescribed range.

When the remeasuring control unit 60 determines that the residual power is within the prescribed range (YES in step SB8), the examiner H2 determines the prescription value of the power of the spectacle lens worn by the subject H1 (step SB9).

Effects of First Embodiment

As described above, in the ophthalmologic system 9 according to the first embodiment, the wavefront sensor 20 is detachably couplable to the opening part 23a of the second examination window 23 of the existing phoropter 14. Therefore, the wavefront sensor 20 may be used integrally with the existing phoropter 14 as necessary. As a result, the measurement result of the wavefront sensor 20 may be swiftly fed back to the existing phoropter 14. Moreover, because the wavefront sensor 20 may be coupled to the existing phoropter 14, cost of the ophthalmologic system 9 can be reduced. In addition, it is possible to meet the needs of both the users who require the wavefront sensor 20 and the users who do not require the wavefront sensor 20.

Even in a case where both the subject eyes E view the visual target chart 13, the aberration characteristics (S, C, A, and high-order aberration) of both eyes may be measured by coupling the wavefront sensors 20 to the existing phoropters 14. Further, the measurement may be performed in real time and in a continuous manner. Thus, it is possible to obtain dynamic aberration characteristics of both the subject eyes E.

Second Embodiment

Figure 8:
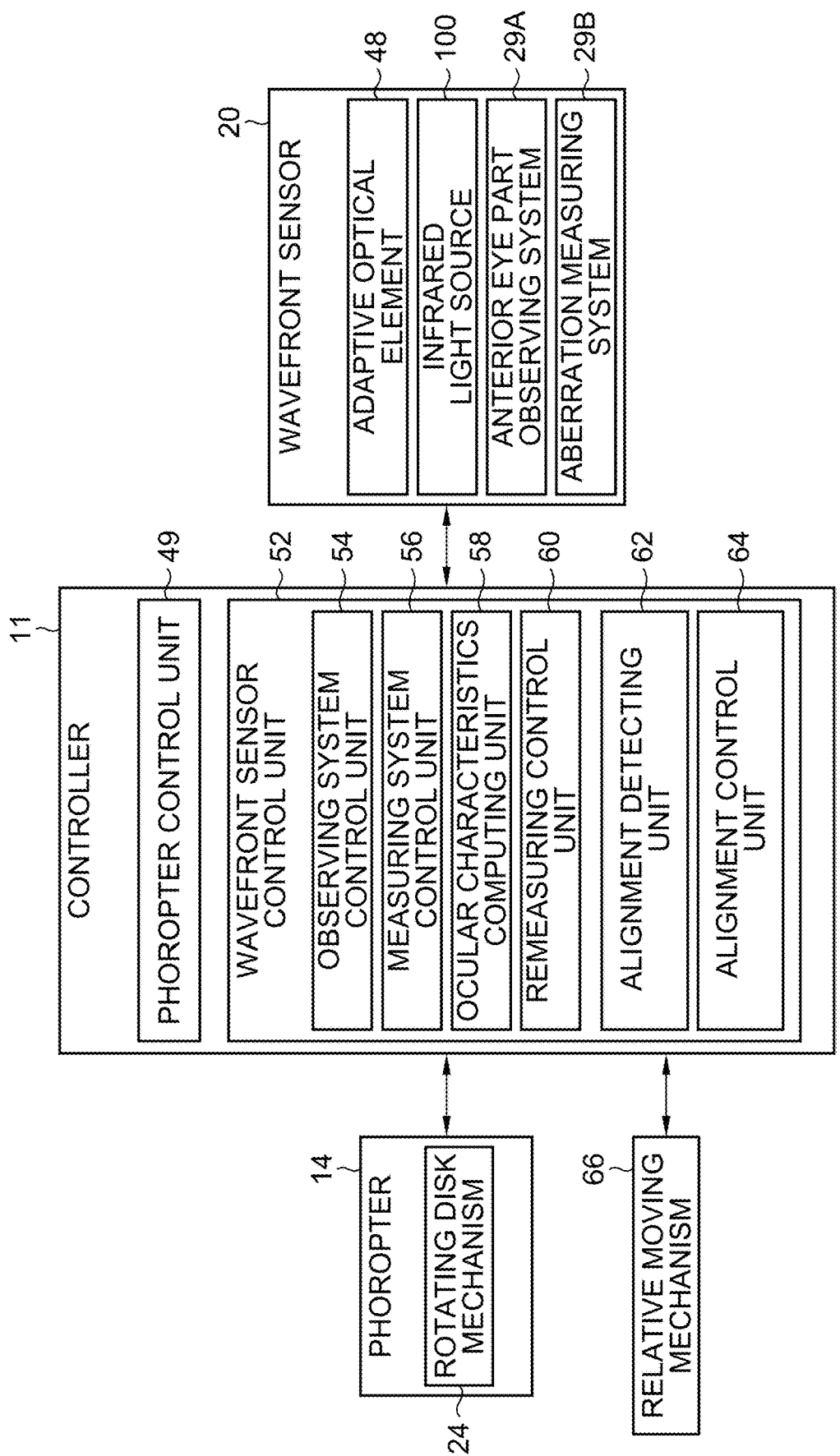
FIG. 8 is a functional block diagram of a controller constituting the ophthalmologic system according to a second embodiment.

FIG. 8 is a functional block diagram of the controller 11 constituting the ophthalmologic system 9 according to a second embodiment. In the first embodiment, alignment of the wavefront sensors 20 with respect to the right and left subject eyes E is performed manually. In the second embodiment, the alignment is performed automatically.

As shown in FIG. 8, the ophthalmologic system 9 of the second embodiment is basically similar in configuration to the ophthalmologic system 9 according to the first embodiment except that the controller 11 is connected to a relative moving mechanism 66 and that the wavefront sensor control unit 52 functions as an alignment detecting unit 62 and an alignment control unit 64 in addition to functioning as other units described above (see FIG. 6). Accordingly, the component members identical in function or configuration to those in the first embodiment are designated by identical reference numerals and the description thereof is omitted.

The relative moving mechanism 66 is, for example, an actuator provided in at least one of a face supporting part (chin receiver) that supports the face of the subject H1, the optometry table 12, a root of the pole 16, the arm 18, etc. The relative moving mechanism 66 moves the right and left phoropters 14 relative to the subject eyes E in up-down, right-left, and anteroposterior directions. This makes it possible to move the wavefront sensors 20 in the up-down, right-left, and anteroposterior directions integrally with the respective phoropters 14.

The alignment detecting unit 62 performs alignment detection that detects relative positional relationship between the subject eye E and the wavefront sensor 20 for each of the right and left subject eyes E, based on an observation image of the anterior eye part of the subject eye E (including an image of alignment flux radiated to the anterior eye part by the alignment optical system 34) obtained by the anterior eye part observing system 29A. For example, the alignment detecting unit 62 detects alignment of the wavefront sensor 20 with the subject eye E in the up-down and right-left directions based on the position of the image of the alignment flux in the observation image, and detects alignment of the wavefront sensor 20 in the anteroposterior direction based on a focusing state of the observation image. Here, since the specific alignment detection method is publicly known technology, the description thereof is omitted herein. The alignment detecting unit 62 then outputs the alignment detection result to the alignment control unit 64.

Based on the alignment detection result input from the alignment detecting unit 62, the alignment control unit 64 drives the relative moving mechanism 66 to perform alignment of the wavefront sensor 20 with the subject eye E for each of the right and left subject eyes E. Thus, it is possible to perform automatic alignment (auto-alignment) of the wavefront sensors 20 with respect to the right and left subject eyes E.

Third Embodiment

Figure 9:
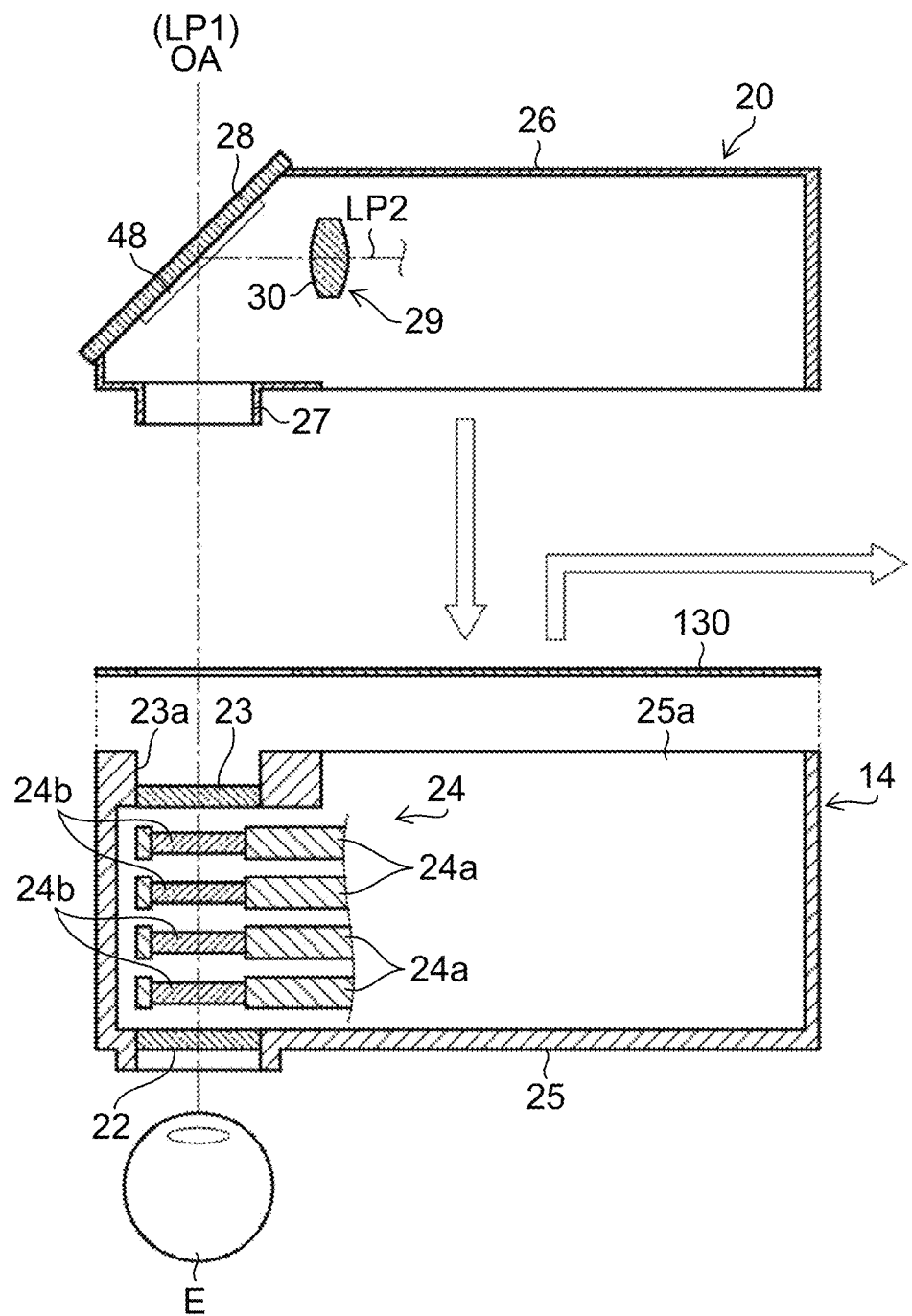
FIG. 9 is a sectional view of a phoropter and a wavefront sensor constituting the ophthalmologic system according to a third embodiment, in a state before the wavefront sensor is coupled to the phoropter.
Figure 10:
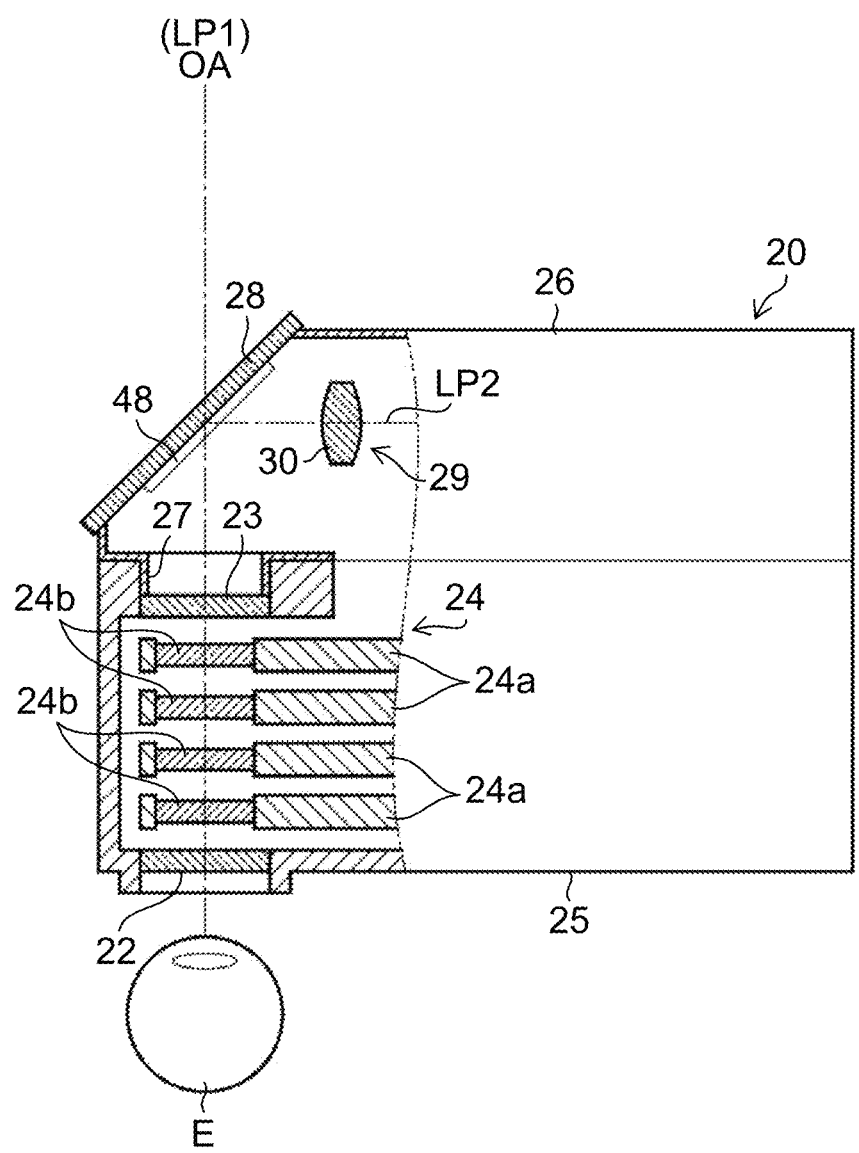
FIG. 10 is a sectional view of the phoropter and the wavefront sensor constituting the ophthalmologic system in the third embodiment, in a state where after the wavefront sensor is coupled to the phoropter.

FIG. 9 is a sectional view of the phoropter 14 and the wavefront sensor 20 provided in the ophthalmologic system 9 according to a third embodiment, in a state before the wavefront sensor 20 is coupled to the phoropter 14. FIG. 10 is a sectional view of the phoropter 14 and the wavefront sensor 20 constituting the ophthalmologic system 9 according to the third embodiment, in a state after the wavefront sensor 20 is coupled to the phoropter 14. Here, since the phoropters 14 and the wavefront sensors 20 have a symmetrical structure, description is given by taking as an example the phoropter 14 and the wavefront sensor 20 corresponding to the right eye of the subject eyes E in FIGS. 9 and 10.

As shown in FIGS. 9 and 10, in the third embodiment, in a state where the wavefront sensor 20 is coupled to the phoropter 14, the sensor housing 26 of the wavefront sensor 20 is used as the rear side surface of the phoropter housing 25, on the side of the second examination window 23. Note that the third embodiment is basically similar in configuration to each of the above embodiments except that the shapes of the phoropter housing 25 and the sensor housing 26 are partially different from the above embodiments. Accordingly, the component members identical in function or configuration to those in each of the above embodiments are designated by identical reference numerals and the description thereof is omitted.

The phoropter housing 25 in the third embodiment is detachably equipped with a rear cover 130 that constitutes the rear side surface on the side of the second examination window 23. The rear cover 130 is detached from the phoropter housing 25 before the wavefront sensor 20 is coupled to the phoropter 14.

The sensor housing 26 in the third embodiment covers a housing body opening part 25a of the phoropter housing 25 so as to function as a substitute of the rear cover 130, in a case where the wavefront sensor 20 is coupled to the phoropter 14 after the rear cover 130 is detached from the phoropter housing 25. Thus, it is possible to integrate the phoropter 14 and the wavefront sensor 20. As a result, the wavefront sensor 20 is prevented from being misaligned due to external contact.

Another Embodiment of Wavefront Sensor

Figure 11:
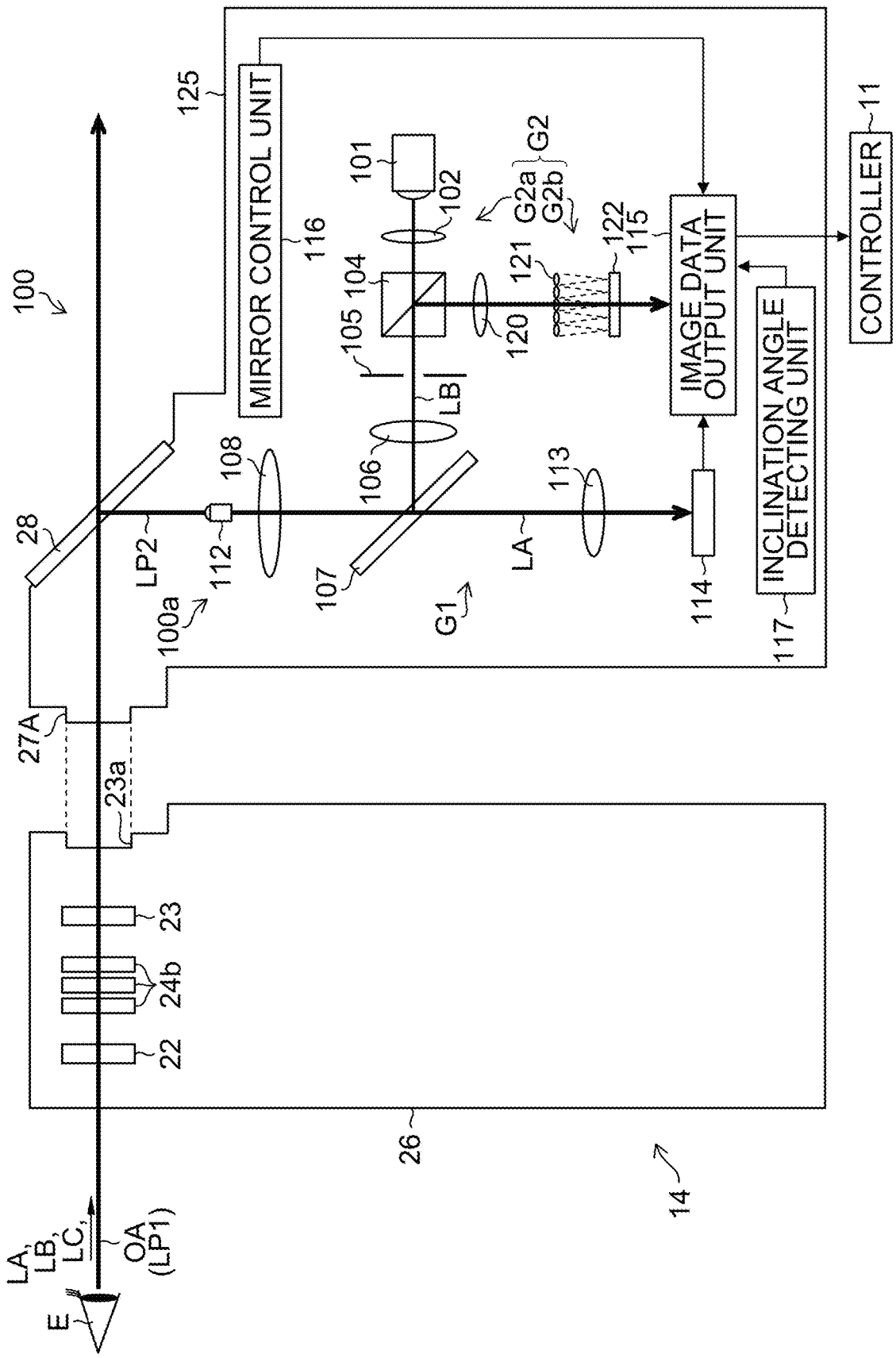
FIG. 11 is a schematic diagram of an optical system of the wavefront sensor according to another embodiment corresponding to the right eye of the subject eyes.

FIG. 11 is a schematic diagram of an optical system of the wavefront sensor 100 corresponding to the right eye as the subject eye E, according to another embodiment. Here, since the optical systems of the right and left wavefront sensors 100 have a symmetrical structure, the structure of the optical system of the wavefront sensor 100 corresponding to the right eye as the subject eye E is described herein. Moreover, the component members identical in function or configuration to those in each of the above embodiments are designated by identical reference numerals and the description thereof is omitted. Furthermore, although the phoropter 14 in FIG. 11 is identical to the phoropter 14 described in each of the above embodiments, illustration of some component members is omitted to prevent complication of the drawing.

The wavefront sensor 100 includes a dichroic mirror 28 common to each of the above embodiments, and a wavefront sensor body 100a different from each of the above embodiments. In FIG. 11, illustration of the adaptive optical element 48 provided in the dichroic mirror 28 is omitted.

The sensor housing 125 of the wavefront sensor 100 holds the dichroic mirror 28 and also houses the wavefront sensor body 100a. In the sensor housing 125, a coupling member 27A that can detachably be coupled to the opening part 23a of the second examination window 23 of the phoropter 14 is also formed. The coupling member 27A is basically the same as the coupling member 27 in each of the above embodiments. Thus, it is possible to detachably couple the wavefront sensor 100 to the phoropter 14, as in each of the above embodiments.

The dichroic mirror 28 (second optical element of the present invention) is held by the rear side surface of the sensor housing 125 at a position facing the coupling member 27A in a state where the dichroic mirror 28 is inclined with respect to the optical axis OA. Because the dichroic mirror 28 is arranged at the position that is on the optical axis OA and that faces the second examination window 23 when the coupling member 27A is coupled to the opening part 23a, the second optical path LP2 is branched from the first optical path LP1 along the optical axis OA.

As in the first embodiment, the dichroic mirror 28 allows visible light to pass through and reflects near-infrared light that is different in wavelength from the visible light. Therefore, the dichroic mirror 28 reflects near-infrared light LB, which is incident from the wavefront sensor body 100a, toward the subject eye E. The dichroic mirror 28 also reflects near-infrared lights LA and LB, which are incident from the subject eye E through the phoropter 14, toward the wavefront sensor body 100a.

The wavefront sensor body 100a emits the near-infrared light LB toward the dichroic mirror 28. The wavefront sensor body 100a also receives the near-infrared lights LA and LB of two wavelengths which are reflected by the dichroic mirror 28, and outputs a light receiving signal for each wavelength region to the controller 11.

The wavefront sensor body 100a includes: an infrared light source 112; an objective lens 108; a dichroic mirror 107; an anterior eye part observing system G1; a light source system G2a and a light receiving system G2b constituting an aberration measuring system G2; an image data output unit 115; a mirror control unit 116; and an inclination angle detecting unit 117. Here, the infrared light source 112 and the inclination angle detecting unit 117 may be omitted.

The infrared light source 112 is a light emitting diode (LED) that emits infrared light (near-infrared light LA) with a wavelength of 940 nm to 950 nm, for example. Two infrared light sources 112 are arranged at positions that face the dichroic mirror 28 to radiate the near-infrared light LA toward the dichroic mirror 28. Accordingly, the near-infrared light LA is radiated to the subject eye E through the dichroic mirror 28 and one or more trial lenses 24b of the phoropter 14 and the like. The return light of the near-infrared light LA coming from the subject eye E travels backward along the same path as an outbound path and enters the objective lens 108.

The objective lens 108 emits the near-infrared light LB with a wavelength of 840 nm, which is incident from the later-described light source system G2a, toward the dichroic mirror 28. The near-infrared lights LA and LB of two wavelengths, reflected by the subject eye E, enter the objective lens 108 after passing through the first optical path LP1, the dichroic mirror 28, and the second optical path LP2. The near-infrared lights LA and LB pass through the objective lens 108 and enter the dichroic mirror 107.

The dichroic mirror 107 allows the near-infrared light LA with a wavelength of 940 nm to 950 nm to pass through, and reflects the near-infrared light LB with a wavelength of 840 nm. Accordingly, the dichroic mirror 107 reflects the near-infrared light LB, which is incident from the later-described light source system G2a, toward the objective lens 108. The dichroic mirror 107 also allows the near-infrared light LA, out of the near-infrared lights LA and LB of two wavelengths incident from the objective lens 108, to enter the anterior eye part observing system G1, and reflects the near-infrared light LB toward the lens system 106. The reflected light in a visible band region coming from the subject eye E passes through the dichroic mirror 28 and exits from the wavefront sensor 100.

The anterior eye part observing system G1 includes a lens system 113 and an imaging element 114.

The lens system 113 is an optical system formed by combining a plurality of lenses, although the lens system 113 is simplified in the drawing. This also applies to other lens systems described later. The lens system 113 images the near-infrared light LA, which is incident from the dichroic mirror 107, to the receiving surface of the imaging element 114.

The imaging element 114 is a publicly known area sensor, such as, for example, a charge coupled device (CCD)-type image sensor. The imaging element 114 receives (images) the near-infrared light LA imaged by the lens system 113, and outputs to the image data output unit 115 a light receiving signal indicating an observation image of the anterior eye part of the subject eye E.

The light source system G2a includes a light source 101, a lens system 102, a polarized beam splitter 104, a diaphragm 105, and a lens system 106.

The light source 101 is a laser diode that emits near-infrared light LB with a wavelength of 830 nm to 840 nm. The lens system 102 changes the near-infrared light LB, incident from the light source 101, into substantially parallel light, and then, emits the light toward the polarized beam splitter 104.

The polarized beam splitter 104 allows S-polarized light to pass through and reflects P-polarized light, for example. The polarized beam splitter 104 allows the near-infrared light LB, which is incident from the lens system 102, to pass through toward the diaphragm 105. As a result, the near-infrared light LB is radiated to the subject eye E after passing through the diaphragm 105, the lens system 106, the dichroic mirror 107, the objective lens 108, the dichroic mirror 28, the phoropter 14, etc. The near-infrared light LB (return light) reflected by the subject eye E travels backward along the same path as an outbound path and enters the polarized beam splitter 104.

The polarized beam splitter 104 reflects the near-infrared light LB (P-polarized light), which is incident from the objective lens 108, toward the lens system 120 in the light receiving system G2b.

The light receiving system G2b shares the polarized beam splitter 104 with the light source system G2a, and includes a lens system 120, a Hartmann plate 121 and an imaging element 122.

The lens system 120 emits the near-infrared light LB, which is incident from the polarized beam splitter 104, toward the Hartmann plate 121.

On the surface of the Hartmann plate 121, a number of microlenses having an equal focal length are formed. The Hartmann plate 121 splits the near-infrared light LB, which is incident from the lens system 120, into a plurality of luminous fluxes corresponding to the respective microlenses, and each luminous flux is imaged on the light receiving surface of the imaging element 122.

The imaging element 122 is a publicly known area sensor, such as, for example, a complementary metal oxide semiconductor (CMOS) image sensor. The imaging element 122 receives (images) the plurality of luminous fluxes imaged on the light receiving surface by the Hartmann plate 121, and outputs to the image data output unit 115 light receiving signals indicating a plurality of point images corresponding to the respective luminous fluxes. Thus, it is possible to measure the wavefront aberration of the subject eye E indicating the ocular characteristics (such as the eye refractivity) of the subject eye E.

The image data output unit 115 outputs image data on an observation image of the anterior eye part of the subject eye E based on the light receiving signals input from the imaging element 114 and image data on the Hartmann image based on the light receiving signals input from the imaging element 122 to the controller 11. Note that the image data output unit 115 may output to the controller 11 image data obtained by combining the image data on the observation image of the anterior eye part and the image data on the Hartmann image. As a result, it is possible to obtain the anterior eye image so that the examiner H2 may visually understand a state of wavefront aberration based on partial color difference. Therefore, the exact pupil center can be set as the origin of the wavefront aberration indication.

Furthermore, it is also possible to measure corneal topography when a placido disk (illustration omitted) that is a corneal topography measurement member is attached to the wavefront sensor 100. In this case, the image data output unit 115 has a function to output the measured corneal topography data in conjunction with the wavefront information.

The mirror control unit 116 drives an actuator, which is not illustrated, for rotating the dichroic mirror 28 left or right so as to control the rotation of the dichroic mirror 28. The mirror control unit 116 also detects a rotation angle of the dichroic mirror 28 via a rotary encoder not illustrated, and outputs the detection result to the image data output unit 115. Thus, it is possible to change a coordinate axis (coordinate system) of the measurement result of the light receiving system G2b and perform data conversion so as to obtain appropriate data in the light receiving system G2b.

The inclination angle detecting unit 117 includes an inclination angle sensor that detects an inclination angle of the wavefront sensor 100. Based on the detection result, the inclination angle detecting unit 117 outputs information on the inclination angle to the image data output unit 115. Thus, it is possible to change the coordinate axis (coordinate system) of the measurement result of the light receiving system G2b and perform data conversion so as to obtain appropriate data in the light receiving system G2b.

Others

In each of the embodiments, the wavefront sensor 20 includes the anterior eye part observing system 29A. However, the anterior eye part observing system 29A may be omitted. In other words, the ophthalmologic device of the present invention also includes devices without the observation system.

In each of the embodiments, the ophthalmologic device of the present invention includes the controller 11 and each of the wavefront sensors 20. However, the ophthalmologic device of the present invention may include only the wavefront sensors 20. In this case, the wavefront sensor control unit 52 (which may include the power determining unit 50) is provided integrally with each of the wavefront sensors 20 or incorporated in the wavefront sensors 20, and the wavefront sensor control unit 52 is connected to the controller 11 in a wired or wireless manner.

In each of the embodiments, the present invention has been described by taking the ophthalmologic system 9 used to determine the prescription value of the spectacle lenses and other lenses to be worn by the subject H1, as an example. However, the present invention is also applicable to the ophthalmologic system 9 used for other applications.

In each of the embodiments, the coupling members 27 and 27A are detachably coupled to the second examination window 23 of each of the phoropters 14. However, component members, such as hole parts, recessed parts, projecting parts and protrusions, provided on the rear side surface of the phoropter housing 25 opposite to the side facing the subject eye E, may be used as coupled members, and various coupling members may detachably be coupled to the coupled members. In this case, the coupled members and the coupling members may be provided at positions different from the positions in each of the above embodiments.

In each of the above embodiments, the wavefront sensor 20 has been described as an example of the ophthalmologic device (objective measuring system) of the present invention as 20. However, the phoropters 14 may be coupled to various types of publicly known objective measuring systems such as reflectometers that measure the eye refractivity of the subject eye E, keratometers that measure the corneal topography of the subject eye E, auto kerato-refractometers that measure the eye refractivity and corneal topography, fundus cameras that take a fundus photograph of the subject eye E, and three-dimensional fundus image photographing devices that acquire a tomographic image of the subject eye E and the like.

EXPLANATION OF REFERENCES

9: ophthalmologic system
11: controller
14: phoropter
20: wavefront sensor
22: first examination window
22: second examination window
23: opening part
24: rotating disk mechanism
24a: lens disk
24b: trial lens
25: phoropter housing
26: sensor housing
27, 27A: coupling member
28: dichroic mirror
29: wavefront sensor body
29A: anterior eye part observing system
29B: aberration measuring system
49: phoropter control unit
50: power determining unit
51: disk mechanism control unit
52: wavefront sensor control unit
54: observing system control unit
56: measuring system control unit
58: ocular characteristics computing unit
60: remeasuring control unit
62: alignment detecting unit
64: alignment control unit
66: relative moving mechanism
99: infrared light source
130: rear cover

What is claimed is:

1. An ophthalmologic device to be coupled to a correcting device configured to correct a visual function of subject eyes, the correcting device including a right-left pair of two examination windows arranged along respective optical axes and a right-left pair of arrangement mechanisms that each arrange one or more first optical elements between the two examination windows, the two examination windows include a right-left pair of first examination windows which are eyepiece windows that face each subject eye and are arranged on a first side surface of the correcting device and a right-left pair of second examination windows arranged on a second side surface of the correcting device opposite to the first side surface of the correcting device, the correcting device further including a right-left pair of openings on the second side surface of the correcting device that each surround a corresponding second examination window, the ophthalmologic device comprising:

- a coupling member configured to be detachably coupled to each of the openings on the second side surface of the correcting device that each surround a corresponding second examination window, the openings being provided on the second side surface of the correcting device on a side opposite to the first side surface of the correcting device that is configured to face each subject eye;
- a second optical element arranged at a position facing the second examination window opposite to the first examination window which is the eyepiece window for each subject eye, in a case where the coupling member is coupled to the opening on the second side surface of the correcting device, the second optical element configured to branch a second optical path from a first optical path along the optical axes; and
- an objective measuring system arranged on the second optical path and configured to acquire ocular characteristics of each subject eye wherein a center of the first examination window and a center of the second examination window are arranged along a same line.

2. The ophthalmologic device according to claim 1, comprising
a housing which is configured to house the second optical element and the objective measuring system, and used as a substitute for a rear cover in a case where the coupling member is coupled to the second examination window in a state where the rear cover which forms a side surface of the correcting device on a side where the second examination window is provided, is detached from the correcting device.

3. The ophthalmologic device according to claim 1, wherein
the second optical element is provided for each of the right and left optical axes,
the second optical element is arranged on an optical axis for each of the right and left optical axes, and
the second optical elements are configured to branch the second optical paths from the first optical paths in directions which are parallel to a plane containing both the optical axes and in which second optical paths for the right and left optical axes are away from each other.

4. The ophthalmologic device according to claim 1, comprising
an output unit configured to output the ocular characteristics acquired by the objective measuring system to a drive control unit configured to control drive of each of the arrangement mechanisms.

5. The ophthalmologic device according to claim 1, comprising:
an observing system configured to acquire an observation image of an anterior eye part of each subject eye; and
an alignment detecting unit configured to detect relative positional relationship between each subject eye and the ophthalmologic device based on the observation image acquired by the observing system.

6. The ophthalmologic device according to claim 5, comprising
an alignment control unit connected to a relative moving mechanism that moves one of each subject eye and the correcting device relatively to the other, the alignment control unit configured to drive the relative movement mechanism based on a detection result of the alignment detecting unit so as to perform alignment of the ophthalmologic device with respect to each subject eye.

7. An ophthalmologic system, comprising:
a correcting device configured to correct a visual function of each subject eye, the correcting device including a right-left pair of two examination windows arranged along respective optical axes, and a right-left pair of arrangement mechanisms which each arrange one or more first optical elements between the two examination windows; and
the ophthalmologic device according to claim 1.

8. The ophthalmologic device according to claim 1, wherein the coupling member is configured to fit within the corresponding opening on the second side surface of the correcting device.

* * * * *